United States Patent [19]
Bens

[11] Patent Number: 5,259,394
[45] Date of Patent: Nov. 9, 1993

[54] ENDOCARDIAC LEAD HAVING AN ACTIVE FASTENING MEANS

[75] Inventor: Jean-Luc Bens, Bethune, France

[73] Assignee: ELA Medical, Montrouge, France

[21] Appl. No.: 812,696

[22] Filed: Dec. 23, 1991

[51] Int. Cl.$^5$ ............................................. A61N 1/05
[52] U.S. Cl. ................................. 607/127; 607/122
[58] Field of Search ................. 128/784, 785, 786, 642

[56] References Cited

U.S. PATENT DOCUMENTS

| | | | |
|---|---|---|---|
| 4,217,913 | 8/1980 | Dutcher | 128/785 |
| 4,280,512 | 7/1981 | Karr et al. | 128/785 |
| 4,917,106 | 4/1990 | Olivier | 128/785 |

FOREIGN PATENT DOCUMENTS

| | | |
|---|---|---|
| 9619 | 2/1980 | European Pat. Off. . |
| 149431 | 7/1985 | European Pat. Off. . |
| 296001 | 12/1988 | European Pat. Off. . |
| 2310775 | 12/1976 | France . |

Primary Examiner—William E. Kamm
Assistant Examiner—Scott M. Getzow
Attorney, Agent, or Firm—Davis Hoxie Faithfull & Hapgood

[57] ABSTRACT

An endocardiac lead of the type including a conductive spiral winding 2 placed inside a sheath 1 made of a flexible material being insensitive to body fluids. This spiral winding 2 is electrically connected to an electrode 3 intended for being brought into contact with the inner wall of the heart. The electrode 3 is hollow and accommodates along its centerline a deformable helix 6 intended for fastening the lead into the heart muscle. The inner diameter of the electrode 3 is smaller than the outer diameter of the undeformed helix 6. The helix 6 presents a sufficient longitudinal elasticity modulus for being retractable inside the electrode 3 with a mechanical deformation, while the helix will substantially recover its initial shape during its extraction out of the electrode and secure the electrode to the tissue. The helix 6 may be made of a nickel-titanium based alloy. The inner wall of the electrode 3 presents a deformation having the shape of a notch 13 against which the helix 6 will abut during its extraction.

35 Claims, 1 Drawing Sheet

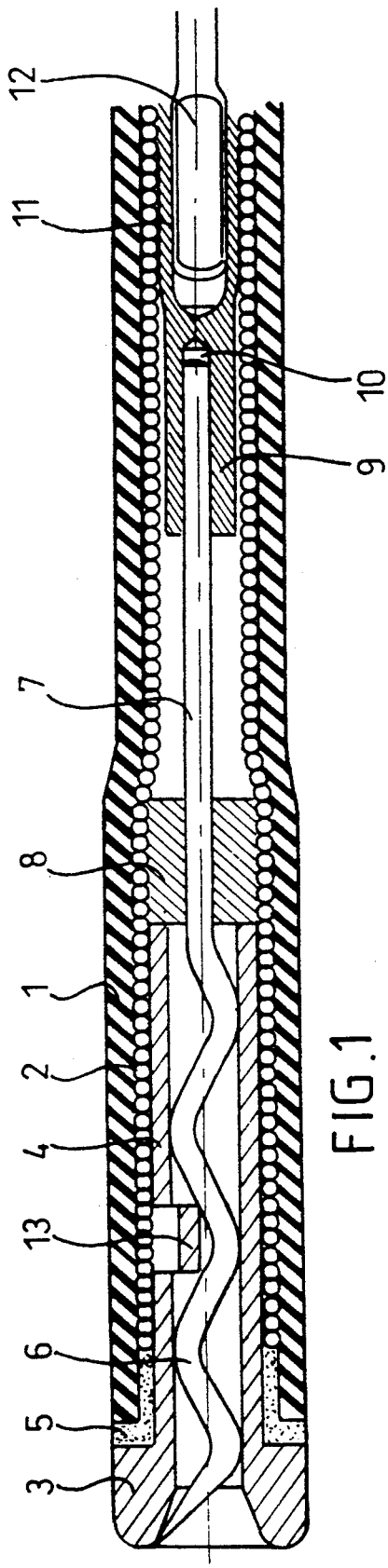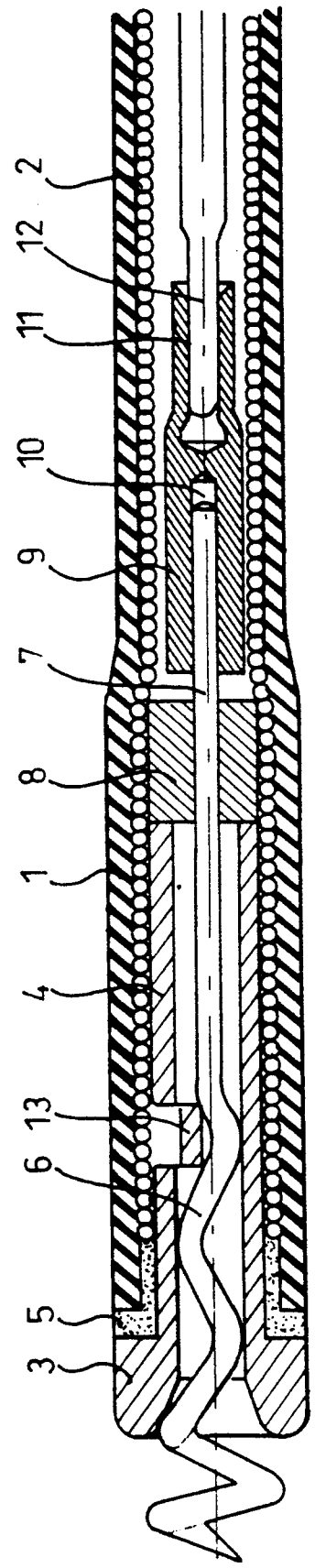

ENDOCARDIAC LEAD HAVING AN ACTIVE FASTENING MEANS

FIELD OF THE INVENTION

The present invention relates to endocardiac leads for cardiac pacemakers, more particularly to leads of the type having their distal end provided with an active fastening means which penetrates into the heart muscle.

BACKGROUND OF THE INVENTION

It is known to use endocardiac leads, also called catheters, for stimulating a heart and for sensing electrical signals therefrom.

An endocardiac lead presents two ends. One end is called the proximal end and is connected within the connector head of a pacemaker to a source of electrical energy. The other end is called the distal end and is typically brought into contact with the internal wall of the heart muscle. The distal end includes a conductive electrode that is connected to an electrically conductive part, such as a coiled conductive wire, encased in a flexible sheath. The sheath may be made, for instance, of silicone rubber.

Endocardiac leads are typically introduced within the heart through a vein, for example, the cephalic vein. When the lead has to be placed inside the atrium, the walls of which are relatively smooth, it is advantageous to provide an active fastening means in the distal end to secure the distal end to the tissue. One known fastening means is a helix shape that is, for example, inserted into the cardiac tissue through rotation.

It is known to provide an endocardiac lead with a helix that is secured to, and protrudes from, the distal end. In this device, when the distal end of the lead has been brought by the surgeon to the desired location inside the atrium, lead is rotated so that the helix penetrates the tissue to fix the distal end in position. One problem with this device is that the protruding helix may, during insertion or rotation of the lead, cause wounds in the vein, or catch on the cardiac valves, complicating the procedure.

It has also been suggested to provide on the distal end a retractable helix. Such a helix is placed in a retracted position within the distal end while the lead is being inserted. The lead is provided with means for causing the helix to rotate and protrude out into tissue, after the lead has been suitably placed.

U.S. Pat. No. 4,217,913 refers to placing the helix within the distal end of the lead and connecting it to a cylindrical actuating end piece that is accommodated within the lead. The end piece is provided with a slit for cooperating with a stylet introduced into the lead for rotating the helix through the intermediary of the end piece. When pulling the lead out, the helix rests against a monofilament which extends radially across the lead while its ends are thermowelded to the external surface of the lead. A drawback of this construction is that the diameter of the lead at the distal end is large compared to the proximal portions of the lead and to leads not having a retractable helix. Another drawback is that it is complicated to manufacture.

The known leads comprising a retractable helix fastening means have, at least at their distal end an undesirably and comparatively large diameter. This is a not an insignificant drawback during an invasive procedure such as the insertion of the lead through a vein. It also is a problem in connection with rotatably driving the helix fastening means. This is because constrictions which are locally compressing the lead in a radial direction are also hindering the rotation of the means for actuating the fastening means.

There is thus a continuing need for improved endocardiac leads that can be secured to tissue, more particularly for such leads that are easier to insert and install in the desired tissue location. There is also a need for an improved fastening means for tightly securing tissue contacting portions of medical devices, catheters and probes to selected tissue sites.

SUMMARY OF THE INVENTION

It is, therefore, an object of the present invention to provide an improved fastening means that can be easily actuated to secure a structural body to tissue.

It is another object to provide an endocardiac lead with an improved fastening means for securing the distal end to cardiac tissue, particularly smooth atrial tissue.

It is another object of the invention to provide an endocardiac lead with a helical fastening means having a reduced diameter during insertion as compared to prior known similar devices.

It is another object to provide a helical fastening means for securing a catheter, such as an endocardiac lead, to tissue that can be easily controlled and brought into place from the outside. It is another object to provide such a fastenable catheter with a minimum number of parts for guiding and supporting the helix to provide for simplified construction and manufacture.

The present invention provides an improved fastener for securing a body to tissue which has reduced size that facilitates placement and fastening. Broadly, the invention concerns apparatus and methods for fastening a body to tissue using a deformable helix that is mechanically deformed in a retracted position inside the body and, once the body is placed adjacent the tissue to which it is to be fastened, can be rotated so that it extends out the body, returns to its natural undeformed shape, and passes into the tissue in its undeformed shape to secure the body to the tissue.

One aspect of the invention is directed to an endocardiac lead of the type comprising a sheath made of flexible material, a conductive spiral winding accommodated within the sheath, an electrode having a hollow passageway, and a deformable helical member that can be retracted into the passageway inside the electrode in a deformed configuration, and extended out the passageway where it assumes essentially and substantially its undeformed configuration. The sheath is preferably electrically insulating and insensitive to the body fluids. The spiral winding is electrically connected at one end to the electrode which is to be brought into contact with the internal wall of the heart and connectable at the other end to a pacemaker.

The electrode passageway has a centerline for receiving the deformable helix that is to be used for fastening the lead into the heart muscle, more specifically the electrode against the tissue. The internal diameter of the electrode is smaller than the natural, undeformed external diameter of the helix.

The helix is made of a material that has a sufficient modulus of longitudinal elasticity for being retractable within the electrode with an elastic mechanical deformation. In other words, the helix will substantially recover its initial shape when extracted out of the electrode and retain sufficient resilience to secure the lead to the tissue. The helix may be made of a plastic or metallic material, more preferably a nickel-titanium based alloy, for example, 55-Nitinol, 60-Nitinol and other nitinol alloys.

In the preferred embodiment, the extraction of the helix out the electrode is effected by a rotary motion imparted by a driving means inserted inside the lead which cooperates with a deformation, for example, a notch, in the inner wall of the passageway against which the helix will rest when retracted and be guided when being extended.

Another aspect of the invention is directed towards apparatus for securing a body to tissue. One such apparatus includes a body having a distal end for contacting tissue and an elongated passageway having an inner dimension;

a deformable helix including a distal tip for penetrating tissue and a proximal driving end for rotating the helix about an axis, the helix having an undeformed configuration including an outer dimension larger the passageway inner dimension; and a mount for securing the helix in a deformed condition inside the elongated passageway for movement therealong so that the helix can be rotated and recover its undeformed shape as it is rotated out of the passageway.

The mount further may include:

a protrusion from extending the passageway for engaging the helix; and a driving end piece, connected to the proximal driving end of the helix, for rotating the helix so that the helix axially moves along the passageway relative to the protrusion.

Preferably, the body distal end has a shaped opening aperture for receiving the helix tip so that the tip is deformed less than the helix turns when the helix is inside the passageway.

Another such apparatus includes an endocardiac lead comprising:

a sheath having a distal end;

a member secured to the distal end of and interior to the sheath having a distal end for contacting tissue and an axial passageway having an inner diameter;

a deformable helix segment having an undeformed shape including an outer diameter that is greater than the inner diameter of the member passageway, an axis of rotation, a distal tip for penetrating tissue, and a proximal end for rotating the helix;

a mount secured inside the sheath for receiving the helix inside the electrode and;

a driving end piece connected to the helix proximal end for rotating the helix relative to the member so that the helix can be deformed as it is retracted in the member and restored to its natural shape as it is extended out the member.

Preferably, the lead includes an electrical conductor interior to the sheath and the member is an electrode in electrical contact with the electrical conductor such that a coating is placed on the helix for electrically insulating the helix from the member and the electrical conductor.

Such a lead may be constructed with the distal end of the sheath having an outer diameter of less than 2.0 mm., the helix having an undeformed outer diameter in the range of 1.2 mm. to 1.4 mm., and the member inner diameter being in the range of 0.6 to 0.7 mm.

Another aspect of the invention is directed towards a method for securing a body having a tissue contacting surface to tissue. One such method includes the steps of:

providing the body with an interior passageway having an inner dimension;

providing a deformable helix having a tip for penetrating tissue and an undeformed shape including an outer dimension that is greater than the passageway inner dimension;

inserting the deformable helix into the passageway so that the helix is elastically deformed;

placing the tissue contacting surface of the body proximate to the tissue to which it is to be secured; and rotating the helix so that it extends out the passageway into the tissue and as it extends out it recovers its undeformed shape.

Preferably, the method includes providing the passageway with a protrusion for engaging the helix inside the passageway so that the helix moves relative to the protrusion during rotation of the helix. In one embodiment, rotating the helix preferably includes:

securing driving end piece to the end of the helix opposite the tip;

providing the driving end piece with a receptacle;

inserting a stylet having a tip into the body so that the stylet tip cooperates with the driving end piece receptacle; and rotating the stylet.

BRIEF DESCRIPTION OF THE DRAWINGS

Further features of the invention, its nature and various advantages will be more apparent from the accompanying drawings and the following detailed description of the invention, in which like reference numerals refer to like elements, and in which:

FIG. 1 is a longitudinal cross-section of the distal end of a lead in accordance with an embodiment of the present invention, showing the helix in a retracted position; and FIG. 2 is a longitudinal cross-section of the distal end of the lead of FIG. 1 showing the helix during its extraction out of the lead.

DETAILED DESCRIPTION OF THE INVENTION

Referring to FIGS. 1 and 2, the distal end of an endocardiac lead according to a preferred embodiment of the present invention is shown. The lead comprises a sheath 1 made of a material, such as a silicone elastomer, that is flexible, insulating and insensitive to the body fluids. Sheath 1 surrounds a helically shaped conductive winding 2. At distal end D, winding 2 is connected to a hollow electrode 3 intended to abut an internal wall of the heart muscle. At proximal end P, winding 2 is connected to a pulse generator constituting the heart stimulator or cardiac pacemaker (not shown). The pulse generator, the cardiac pacemaker and their connection to the endocardiac lead of the described embodiment forms no part of the present invention.

In a preferred embodiment, electrode 3 is substantially annular and comprises a tubular extension 4 which extends inwardly inside the lead so that it will contact a certain number of turns of winding 2, e.g., 8 triple turns, for ensuring the transfer to electrode 3 of the electrical pulses received from the pacemaker. Electrode 3 is fixed to the distal end of the sheath 1 by means of an adhesive 5, for example, silicone adhesive.

The lead has in its distal end D, a fastening means in the form of a helix 6 extending coaxially to electrode 3. The proximal part of helix 6 forms a straight stem 7 which extends through a cylindrical seal 8 made of an electrically insulating material, for example silicon rubber or polyurethane elastomer. The tip of this proximal part is connected to a driving end piece 9 is a conventional manner which is also cylindrical and made of steel and other metallic material, e.g., chrome and cobalt alloy. Preferably, the stem tip is inserted and clamped in a bore 10 formed in driving end piece 9 and the opposite end of driving end piece 9 presents a radial slit 11 for receiving the tip 12 of a conventional stylet.

Stylet tip 12 is flattened, for example, into the shape of a screwdriver, and is introduced into and through the lead to fit in slit 11 for rotating driving end piece 9 and, hence, helix 6. Stylet tip 12, together with the driving end piece 9, thus provides a driving means for rotating helix 6. Stylet tip 12 is typically withdrawn from the lead after the lead has been securely fastened and positioned. The means used during the positioning of the lead and its fastening, including the means for inserting and driving stylet tip 12, also do not form a part of the present invention and thus will not be described in more detail.

An alternate embodiment of the driving means (not shown) may comprise a driving end piece made of an insulating material which is permanently connected to a second winding of material inside the sheath, which may be made of stainless steel. In this embodiment, the second winding is rotated to rotate the driving end means and helix 6, and will remain inside the lead after screwing-in the helix to fasten the lead.

Preferably, helix 6 is electrically insulated, so that the heart will be stimulated solely by the electrode 3. For example, helix 6 may be electrically insulated by application of an insulating coating (not shown) of, for example, a fluorocarbon based material such as TEFLON. Alternatively, it is sufficient to apply a suitable insulating coating on only the distal portion of the helix, namely, that portion which contacts tissue.

In an alternate embodiment, it is possible to stimulate the heart by means of both the electrode and the helix fastener and yet another alternative provides for using a metallic helix as the electrode. In the latter case, the helix would be directly connected to the winding 2 in a suitable, conductive manner and the "electrode 3" may be made of or coated with an insulating material.

In the preferred embodiment, the lead is provided with and mount means for retaining helix 6 inside electrode 3 and for providing a buttress means against which helix 6 may rest. These means preferably comprise a notch 13 which extends inwardly from the inner wall of electrode 3 in the electrode passageway and cooperates with the helix turns. Notch 13 may be obtained through a mechanical deformation of the electrode wall, use of a set screw or pin passing through the electrode wall, or the like. Notch 13 is thus intended on the one hand to retain helix 6 in place in a retracted position inside electrode 3 as illustrated in FIG. 1, and on the other hand to provide a buttress support for helix 6, so that helix 6 may be axially displaced along the passage as it is rotated. In place of a protrusion, the mount could be a stationary threaded section in the lead distal end that corresponds either with the turns of the helix or a corresponding threaded portion on either stem 7 or driving end piece 9.

In accordance with the present invention, helix 6 is made of a material which presents a high modulus of longitudinal elasticity, such as, for example, a plastic or metallic material, preferably a metallic alloy having a titanium-nickel base, more preferably a nitinol. Such an alloy affords an elongation of on the order of 8% compared to stainless steel, for which the accepted elongation is only 0.3%, which gives the possibility of obtaining much shorter radii of curvature with the Ti-Ni alloy as compared to stainless steel helix of the prior known type.

The high longitudinal elasticity of such an alloy makes it possible to produce helix 6 having an outer diameter that, when extended out of electrode 3, is substantially larger than the inner diameter of annular electrode 3 by a factor of from 1.5 to 2.5, but which may nevertheless be retracted inside electrode 3 while being subjected to a mechanical deformation which results in an elongation of the helix by a factor of from 2 to 3 and a reduction of its outer diameter by a factor of from 1.5 to 2.5. The helix is thus accommodated with a certain degree of prestressing inside the electrode, whereby it will substantially recover its initial, unstressed shape as soon as it emerges again out of the electrode while becoming screwed into the heart muscle tissue.

One suitable helix 6 has been constructed of nitinol alloy in cylindrical wire from having a diameter of 0.2 mm.,and having in its natural undeformed shape 1 turn/mm., an outer diameter of 1.4 mm., a helical length of at least 9.0 mm. as measured axially from the tip along its turns to the distal end of the stem. The tip is sharpened in a conventional manner. Such a helix is suitable for insertion inside an electrode passageway having an inner diameter of 0.7 mm. The sheath of the endocardiac catheter may have an outer diameter of 2.0 mm. suitable for enveloping the electrode and coiled wiring. It should be understood that the dimensions of the lead, electrode, and helix may vary depending on the use to be made of the lead, the tissue to which it is to be secured, the vein or other path through which the lead will be inserted in the body, and the amount of force required to secure the lead (or other structural body) to the tissue site. Also, the cross sectional configuration of the helix wire may be a shape other than a circle.

A deformable helix made of a material with a sufficient modulus of longitudinal elasticity, e.g., nitinol type nickel-titanium alloy may be made by turning the material on a form having a diameter that is smaller than the desired diameter of the undeformed shape of the helix by an amount suitable to compensate for the elasticity of the material. This forming process is conventional.

A helix according to the present invention preferably has the following mechanical characteristics: elongation at breaking point in the range of 10 to 20, preferably 15 to 20%; an acceptable elastic elongation in the range of 6 to 8, preferably 8%; a Young's modulus in the range of 9,000 to 10,000, preferably 9,800 daN/mm$^2$; an elastic limit in the range of 40 to 50, preferably 42 daN/mm$^2$; a Poisson's modulus in the range of 0.30 to 0.35, preferably 0.33; and breakdown point in the range of 80 to 90, preferably 88 daN/mm$^2$. These characterists are measured on the raw material used for form the helix using commonly accepted and performed tests, such as described in TECHNIQUES DE L'INGENIEUR Etude des alliages Tome Ml II 1990, Chapitre: "Essais Mécaniques des métaux. Détermination des lois de Comportement".

Advantageously, the invention provides for a substantial reduction of the diameter of the distal tip of the lead and enhanced maneuverability as compared to prior known leads and retains the advantages of a retracted helix. Consequently, during use, the lead may be more readily introduced into the access vein and the heart, and the distal end of the lead may be more easily directed to rest against the heart muscle in the desired location. Thereafter, helix 6 may be automatically driven out of the electrode as it is caused to rotate by means of stylet tip 12. As helix 6 is driven it will recover its initial shape as it emerges gradually out of the electrode until it reaches its extended position (see FIG. 2), while simultaneously screwing itself into the heart muscle in its undeformed shape. The electrode will thus be properly anchored inside and to the heart and will find itself positively urged towards the inner wall of the heart, thus providing a good electrical contact for the transmission of electric pulses to or from a pacemaker.

The distal end of electrode 3 is preferably provided with a tooled or shaped opening, preferably a chamfered or beveled face. Such an opening provides for retracting helix 6 into electrode 3 so that the helix tip, which is typically provided with a sharpened point and is thus more subjectable to elastic deformation, rests against the shaped surface and is inside the electrode. Advantageously, the helix tip will not be deformed or compressed as much as the remainder of the helix. For example, an electrode having an outer diameter of 2.0 mm and an inner diameter of 0.7 mm may have a chamfer centered about its centerline having a depth of 0.6 mm and an angle of 60 degrees measured relative to the plane of the distal end face of electrode 3. In addition, the shaped face may provide for applying a portion of the energy previously stored by mechanically deforming the helix. In this regard, as the helix extends out, the turns will contract towards the stem and exert a force against the chamfered face. This may reduce the force required to rotate helix 6 out of the electrode passageway. The passageway for receiving the helix is preferably uniform in shape, and more preferably cylindrical. It should be understood, however, that other configurations suitable for receiving a deformable helix under mechanical deformation may be used. Also, it should be understood that in place of the helix and rotating the helix to advance it into the tissue any deformable fastener and means for advancing the fastener into the tissue so that the fastener returns substantially to its undeformed shape to secure the body to the tissue may be used such that the fastener has other than a helical shape and a corresponding cylindrical passageway. Accordingly, the term "dimension" of the passageway and the helix should be understood to mean the maximum distance between opposing surfaces, including, for example, the diameter of a cylindrical cross section, and, for another example, the width of the widest side of a rectangle and the outer boundary of the deformable fastening means in its undeformed shape. It also should be understood that upon penetrating the tissue, the natural shape of the fastener be somewhat distorted as a result of contacting the tissue to secure the body to the tissue.

Although described in the context of endocardiac leads, it should be understood that the deformable active fastening means of the present invention is applicable to other devices or bodies to be secured to tissue, e.g., probes for monitoring physiological parameters, microsurgical instruments and the like.

One skilled in the art will appreciate that the present invention can be practiced by other than the desired embodiments which are presented for purposes of illustration and not of limitation.

I claim:

1. An endocardiac lead of the type comprising a sheath (1), an electrode (3), a helix (6), a conductive spiral winding (2) placed inside the sheath (1) made of a flexible insulating material which is insensitive to body fluids, the spiral winding (2) being electrically connected to the electrode (3) intended for being brought into contact with the inner wall of the heart, said electrode (3) being hollow and receiving along its centerline the helix (6) for fastening the lead into the heart muscle, characterized in that the internal diameter of the electrode (3) is smaller than the external diameter of the helix (6), and in that the helix (6) presents a sufficient modulus of longitudinal elasticity for being retractable within the electrode (3) with a mechanical deformation, and in that the helix (6) will substantially recover its initial shape when being extracted out of the electrode.

2. A lead according to claim 1, characterized in that the helix (6) is made of a metallic alloy.

3. A lead according to claim 2, characterized in that the alloy is a nickel-titanium based alloy.

4. A lead according to claim 1, characterized in that the helix (6) is covered, at least over its distal portion, with an electrically insulating coating.

5. A lead according to claim 4, characterized in that the coating consists of a fluorocarbon based material.

6. A lead according to claim 1, wherein the extraction of the helix (6) out of the electrode (3) is effected through a rotation controlled by a driving means (9, 12) inserted inside the lead, characterized in that the inner wall of the electrode (3) presents a deformation having the shape of a notch (13) against which the helix (6) will rest during its extraction.

7. A lead according to claim 2 wherein the extraction of the helix (6) out of the electrode (3) is effected through a rotation controlled by a driving means (9, 12) inserted inside the lead, characterized in that the inner wall of the electrode (3) presents a deformation having the shape of a notch (13) against which the helix (6) Will rest during its extraction.

8. A lead according to claim 2, characterized in that the helix (6) is covered, at least over its distal portion, with an electrically insulating coating.

9. A lead according to claim 3, characterized in that the helix (6) is covered, at least over its distal portion, with an electrically insulating coating.

10. Apparatus for securing a body to tissue comprising:
- a first body having a distal end for contacting tissue and an elongated passageway having an inner dimension;
- a deformable fastener means for penetrating tissue and securing the first body to the tissue comprising a second body having a distal tip, a proximal driving end, and an undeformed configuration including an outer dimension larger than the passageway inner dimension; and
- a mount means for securing the second body in a deformed condition inside the elongated passageway for rotational movement therealong so that the second body can be rotated and advanced and recover its undeformed shape as it is advanced out of the passageway.

11. The apparatus of claim 10 wherein the second body further comprises a material having a Young's modulus in the range of from 9,000 to 10,000 daN/mm$^2$.

12. The apparatus of claim 10 wherein the second body further comprises an alloy including nickel and titanium.

13. The apparatus of claim 10 wherein the second body further comprises a deformable helix having an axis and wherein the mount means further comprises:
   a protrusion extending from the passageway interior for engaging the deformable helix; and
   a driving end piece connected to the proximal driving end for rotating the deformable helix about the axis thereby to move the deformable helix axially along the passageway relative to the protrusion.

14. The apparatus of claim 13 wherein the driving end piece further comprises an aperture for receiving a stylet tip.

15. The apparatus of claim 13 wherein the first body distal end further comprises a shaped opening for receiving the deformable helix distal tip in the passageway.

16. The apparatus of claim 13 wherein the deformable helix is made of a material characterized by an elongation at breaking point in the range of 10 to 20%, an elastic elongation in the range of 6 to 8%; a Young's modulus in the range of 9,000 to 10,000 daN/mm$^2$; an elastic limit in the range of 40 to 50 daN/mm$^2$; a Poisson's modulus in the range of 0.30 to 0.35; and a breakdown point in the range of 80 to 90 daN/mm$^2$.

17. An endocardiac lead comprising:
   a sheath having a distal end;
   a member secured to the distal end of and interior to the sheath including a distal face for contacting tissue and an axial passageway having an inner diameter;
   a deformable helix having an undeformed shape including an outer diameter that is greater than the inner diameter of the member passageway, an axis of rotation, a distal tip for penetrating tissue, and a proximal end for rotating the helix;
   a mount means secured inside the sheath for receiving the deformable helix inside the member; and
   a driving end piece connected to the helix proximal end for rotating the helix relative to the member so that the helix can be deformed as it is retracted in the member and restored to its natural shape as it is extended out the member.

18. The apparatus of claim 17 further comprising:
   an electrical conductor interior to the sheath;
   a coating on the helix for electrically insulating the helix from the tissue;
   wherein the member further comprises an electrode in electrical contact with the electrical conductor.

19. The apparatus of claim 18 wherein the electrical conductor is spirally wound interior to the sheath.

20. The apparatus of claim 19 wherein the helix is made of a metallic alloy having a Young's modulus of in the range of from 9,000 to 10,000 daN/mm$^2$.

21. The apparatus of claim 17 wherein the member further comprises a protrusion in the passageway for engaging the helix so that the helix moves relative to the protrusion as the helix is rotated.

22. The apparatus of claim 21 wherein the distal end of the sheath has an outer diameter of less than 2.0 mm, the helix has an undeformed outer diameter in the range of 1.2 to 1.4 mm, and the member inner diameter is in the range of 0.6 to 0.7 mm.

23. The apparatus of claim 17 wherein the member further comprises a shaped opening for receiving the deformable helix distal tip in the passageway so that the helix tip is deformed less than the helix when retracted in the member.

24. The apparatus of claim 23 wherein the material is a metallic alloy.

25. The apparatus of claim 24 wherein the metallic alloy is a nickel-titanium alloy.

26. The apparatus of claim 17 wherein the helix is made of a material characterized by an elongation at breaking point in the range of 10 to 20%, an elastic elongation in the range of 6 to 8%; a Young's modulus in the range of 9,000 to 10,000 daN/mm$^2$; an elastic limit in the range of 40 to 50 daN/mm$^2$; a Poisson's modulus in the range of 0.30 to 0.35; and a breakdown point in the range of 80 to 90 daN/mm$^2$.

27. The apparatus of claim 17 wherein the distal end of the sheath has an outer diameter of less than 2.0 mm, the helix has an undeformed outer diameter in the range of 1.2 to 1.4 mm, and the member inner diameter is in the range of 0.6 to 0.7 mm.

28. A method for securing a body having a tissue contacting surface to tissue comprising:
   providing the body with an interior passageway having an inner dimension;
   providing a deformable fastener having a tip for penetrating tissue and an undeformed shape including an outer dimension that is greater than the passageway inner dimension;
   inserting the deformable fastener into the passageway so that it is deformed;
   placing the tissue contacting surface of the body proximate to the tissue to which the body is to be secured; and
   rotating the fastener relative to the body so that it extends out the passageway and penetrates into the tissue and as it extends out it recovers its undeformed shape.

29. The method of claim 28 wherein providing the deformable fastener further comprises providing an deformable helix, the method further comprising providing the passageway with a protrusion for engaging the helix inside the passageway so that the helix moves relative to the protrusion during rotation of the helix.

30. The method of claim 29 wherein rotating the helix further comprises:
   securing a driving end piece to the end of the helix opposite the tip;
   providing the driving end piece with a receptacle;
   inserting a stylet having a tip into the body so that the stylet tip cooperates with the driving end piece receptacle; and
   rotating the stylet.

31. The method of claim 29 wherein providing the deformable helix further comprises forming the helix from a material characterized by an elongation at breaking point in the range of 10 to 20%, accepted elongation in the range of 6 to 8%; a Young's modulus in the range of 9,000 to 10,000 daN/mm$^2$; an elastic limit in the range of 40 to 50 daN/mm$^2$; a Poisson's modulus in the range of 0.30 to 0.35; and a breakdown point in the range of 80 to 90 daN/mm$^2$.

32. The method of claim 28 wherein the fastener is made of a material having a Young's modulus in the range of from 9,000 to 10,000 daN/mm$^2$.

33. The method of claim 28 wherein the fastener is made of a metallic alloy.

34. The method of claim 33 wherein the fastener is made of an alloy of nickel and titanium.

35. The method of claim 28 wherein providing the deformable fastener further comprises forming a fastener from a material characterized by an elongation at breaking point in the range of 10 to 20%, an elastic elongation in the range of 6 to 8%; a Young's modulus in the range of 9,000 to 10,000 daN/mm$^2$; an elastic limit in the range of 40 to 50 daN/mm$^2$; a Poisson's modulus in the range of 0.30 to 0.35; and a breakdown point in the range of 80 to 90 daN/mm$^2$.

* * * * *